(12) United States Patent
Das et al.

(10) Patent No.: US 11,440,894 B2
(45) Date of Patent: Sep. 13, 2022

(54) PROCESS DEVELOPMENT FOR 5-HYDROXYMETHYLFURFURAL (5-HMF) SYNTHESIS FROM CARBOHYDRATES

(71) Applicant: Council of Scientific and Industrial Research, New Delhi (IN)

(72) Inventors: Pralay Das, Palampur (IN); Ajay Kumar, Palampur (IN); Shaifali, Palampur (IN)

(73) Assignee: Council of Scientific & Industrial Research, New Delhi (IN)

( * ) Notice: Subject to any disclaimer, the term of this patent is extended or adjusted under 35 U.S.C. 154(b) by 71 days.

(21) Appl. No.: 17/254,959

(22) PCT Filed: Feb. 14, 2019

(86) PCT No.: PCT/IN2019/050116
§ 371 (c)(1),
(2) Date: Dec. 22, 2020

(87) PCT Pub. No.: WO2019/244166
PCT Pub. Date: Dec. 26, 2019

(65) Prior Publication Data
US 2021/0122722 A1    Apr. 29, 2021

(30) Foreign Application Priority Data
Jun. 22, 2018 (IN) .............................. 201811023331

(51) Int. Cl.
*C07D 307/50* (2006.01)
(52) U.S. Cl.
CPC .................................. *C07D 307/50* (2013.01)
(58) Field of Classification Search
CPC ................................................... C07D 307/50
See application file for complete search history.

(56) References Cited

U.S. PATENT DOCUMENTS

| | | | |
|---|---|---|---|
| 2,750,394 | A | 6/1956 | Peniston |
| 2,851,468 | A | 9/1958 | Snyder |
| 4,590,283 | A | 5/1986 | Gaset et al. |
| 7,317,116 | B2 | 1/2008 | Sanborn |

FOREIGN PATENT DOCUMENTS

EP    2001859 B1    5/2010

OTHER PUBLICATIONS

Aellig et al., "Continuous D-Fructose Dehydration to 5-Hydroxymethylfurfural Under Mild Conditions", ChemSUSChem, vol. 5, pp. 1737-1742, 2012.
Aida et al., "Dehydration of D-glucose in high temperature water at pressures up to 80 MPa", The Journal of Supercritical Fluids, vol. 40, pp. 381-388, 2007.
Benvenuti et al., "Heterogeneous zirconium and titanium catalysts for the selective synthesis of 5-hydroxymethyl-2-furaldehyde from carbohydrates", Applied Catalysts A: General, vol. 193, pp. 147-153, 2000.
Binder et al., "{Simple Chemical Transformation of Lignocellulosic Biomass into Furans for Fuels and Chemicals", J. Am. Chem. Soc., vol. 131, pp. 179-185, 2009.
Bozell et al., "Technology development for the production of biobased products from biorefinery carbohydrates—the US Department of Energy's "Top 10" revisited", Green Chem, vol. 12, pp. 539-544, 2010.
Cao et al., "Production of 5-hydroxymethylfurfural from starch-rich food waste catalyzed by sulfonated biochar", Bioresearch Technology, vol. 252, pp. 76-82, 2018.
Chareonlimkun et al., "Reactions of C5 and C6-sugars, cellulose, and lignocellulose under hot compressed water (HCW) in the presence of heterogeneous acid catalysts", Fuel, vol. 89, pp. 2873-2880, 2010.
Chheda et al., "An overview of dehydration, aldol-condensation and hydrogenation processes for production of liquid alkanes from biomass-derived carbohydrates", Catalysis Today, vol. 123, pp. 59-70, 2007.
Chheda et al., "Production of 5-hydroxymethylfurfural and furfural by dehydration of biomass-derived mono- and poly-saccharides" Green Chemistry, vol. 9, pp. 342-350, 2007.
Corma et al., "Chemical Routes for the Transformation of Biomass into Chemicals", Chem. Rev., vol. 107, pp. 2411-2502, 2007.
Crisci et al., "Bifunctional Solid Catalysts for the Selective Conversion of Fructose to 5-Hydroxymethylfurfural", Top Catal, vol. 53, pp. 1185-1192, 2010.
Fayet, "Nouvelle Methode De Preparation DU 5-Hydroxymethyl-2-Furaldehyde Par Action De Seis D'Ammonium Ou D'Immonium Sur Les Mono-, Oligo- Et Poly-Saccharides Acces Direct Aux 5-Halogenomethyl-2-Furaldehydes", Carbohydrate Research, vol. 122, pp. 59-68, 1983.
Ilgen et al., "Conversion of carbohydrates into 5-hydroxymethylfurfural in highly concentrated low melting mixtures", Breen Chemistry, vol. 11, pp. 1948-1954, 2009.
Kourieh et al., "Relation between surface acidity and reactivity in fructose conversion into 5-HMF using tungstated zirconia catalysts", Catalyst Communications, vol. 30, pp. 5-13, 2013.
Kuster et al.," I he influence of pH and weak-acid aninons on the dehydration of D-fructose", Carbohydrate Research, vol. 54, pp. 185-191, 1977.
Kuster et al., "The influence of the initial and catalyst concentrations on the dehydration of D-fructose", Carbohydrate Research, vol. 54, pp. 165-176, 1977.
Kuster et al., "The influence of water concentration on the dehydration of D. fructose", Carbohydrate Research, vol. 54, pp. 177-183, 1977.

(Continued)

*Primary Examiner* — Golam M Shameem
(74) *Attorney, Agent, or Firm* — Dinsmore & Shohl, LLP

(57) ABSTRACT

The present invention relates to a new protocol for "Process development for 5-hydroxymethylfurfural (5-HMF) synthesis from carbohydrates". A convenient, atom-economic, highly selective and cost-effective process has been developed for the preparation of 5-HMF from cellulose, hemicellulose, starch, different sources of carbohydrates and further extended to glucose and fructose.

7 Claims, No Drawings

(56) References Cited

OTHER PUBLICATIONS

Kuster et al., "Preparation of 5-Hydroxymethylfurfural", Die Starke, vol. 29, pp. 99-103, 1977.
Mednick, "The Acid-Base-Catalyzed Conversion of Aldohexose into 5-(Hydroxymethyl)-2-furfural", J. C. Speck, Adv. Carbohydrate Chem., vol. 39, No. 79, pp. 398-403, 1958.
Mercadier et al., "Syntheis of 5-Hydroxymethyl-2-furancarboxaldehyde Catalysed by Cationic Exchange Resins. Part 1. Choice of the Catalyst and Characteristics of the Reaction Medium", J. Chem. Tech. Biotechnol. vol. 31, pp. 489-496, 1981.
Moliner et al., "Tin-containing zeolites are highly active catalysts for the isomerization of glucose in water", PNAS, vol. 107, No. 4, pp. 6164-6168, Apr. 6, 2010.
Moreau et al., "Preparation of 5-hydroxymethylfurfural from fructose and precursors over H-form zeolites", Industrial Crops and Products, vol. 3, pp. 85-90, 1994.
Moreau et al., "Dehydration of fructose to 5-hydroxymethylfurfural over H.-mordenites", Applied Catalysts A: General, vol. 145, pp. 211-224, 1996.
Newth, "The Formation of Furan Compounds from Hexoses", Department of Chemistry, University College of North Wales, Bangor, North Wales, Adv. Carbohydr. Chem, pp. 83-106, 1951.
Nikolla et al., "One-Pot Synthesis of 5-(Hydroxymethyl)furfural from Carbohydrates using Tin-Beta Zeolite", American Chemical Society, ASC Catal, vol. 1, pp. 408-410, 2011.
Pagan-Torres et al., "Production of 5-Hydroxymethylfurfural from Glucose Using a Combination of Lewis and Bronsted Acid Catalysts in Water in a Biphasic Reactor with an Alkylphenol Solvent", American Chemical Society, ACS Catal. vol. 2, pp. 930-934, 2012.
Qi et al., "Catalytical conversion of fructose and glucose into 5-hydroxymethylfurfural in hot compressed water by microwave heating", Catalysis Communications, vol. 9, pp. 2244-2249, 2008.
Qi et al., "Kinetics of Non-catalyzed Decomposition of Glucose in High-temperature Liquid Water", Chinese Journal of Chemical Engineering, vol. 16, No. 6, pp. 890-894, 2008.
Qi et al., "Fast Transformation of Glucose and Di-/Polysaccharides into 5-Hydroxymethylfurfural by Microwave Heating in an Ionic Liquid/Catalyst System", ChemSusChem, vol. 3, pp. 1071-1077, 2010.
Ranoux et al., "5-Hydroxymethylfurfural Synthesis from Hexoses is Autocatalytic", American Chemical Society, ASC Catal. vol 3, pp. 760-763, 2013.
Richter et al., "Set of Acidic Resin Catalysts to Correlate Structure and Reactivity in Fructose Conversion to 5-Hydroxymethylfurfural", American Chemical Society, ACS Catal vol. 3, pp. 123-127, 2013.
Roman-Leshkov et al., "Phase Modifiers Promote Efficient Production of Hydroxymethylfurfural from Fructose", Science, vol. 312, pp. 1933-1937, Jun. 30, 2006.
Roman-Leshkov et al, "Production of dimethylfuran for liquid fuels from biomass-derived carbohydrates", Nature Letters, vol. 447, pp. 982-986, Jun. 21, 2007.
Roman-Leshkov et al., "Solvent Effects on Fructose Dehydration to 5-Hydroxymethylfurfural in Biphasic Systems Saturated with Inorganic Salts", Top Catal., vol. 52, pp. 297-303, 2009.
Roman-Leshkov et al., "Mechanism of Glucose Isomerization Using a Solid Lewis Acid Catalyst in Water", Angew. Chem. Int. Ed., vol. 49, pp. 8954-8957, 2010.
Shimizu et al., "Enhanced production of hydroxymethylfurfural from fructose with solid acid catalysts by simple water removal methods", Catalysis Communications, vol. 10, pp. 1849-1853, 2009.
Sidhpuria et al., "Supported ionic liquid silica nanoparticles (SILnPs) as an efficient and recyclable heterogeneous catalyst for the dehydration of fructose to 5-hydroxymethylfurfural", Green Chemistry, vol. 13, pp. 340-349, 2011.
Takagaki et al., "One-Pot Synthesis of 2,5-Diformylfuran from Carbohydrate Derivatives by Sulfonated Resin and Hydrotalcite-Supported Ruthenium Catalysts", American Chemical Society, ASC Catal. vol. 1, pp. 1562-1565, 2011.
Tan et al., "Production of 5-hydroxymethyl furfural from cellulose in CrCl2/Zeolite/BMIMCI system", Biomass & Bioenergy, vol. 35, pp. 1367-1370, 2011.
Thananatthanachon et al., "Efficient Production of the Liquid Fuel 2,5-Dimethylfuran from Fructose Using Formic Acid as a Reagent", Angew. Chem. vol. 122, pp. 6766-6768, 2010.
Tucker et al., "Acid-Functionalized SBA-15-Type Periodic Mesoporous Organosilicas and Their Use in the Continuous Production of 5-Hydroxymethylfurfural", American Chemical Society, ACS Catal. vol. 2, pp. 1865-1876, 2012.
Wang et al., "Catalytic hydrolsis of lignocellulosic biomass into 5-hydroxymethylfurfural in ionic liquid", Bioresourse Technology, vol. 102, pp. 4179-4183, 2011.
Werpy et al., "Top Value Added Chemicals from Biomass, vol. 1—Results of Screening for Potential Candidates from Sugars and Synthesis Gas", U.S. Department of Energy, Energy Efficiency and Renewable Energy, 76 pages, Aug. 2004.
Wu et al., "Effect of CO2 on conversion of insulin to 5-hydroxymethylfurfural and propylene oxide to 1,2-propanediol in water", Green Chemistry, vol. 12, pp. 1215-1219, 2010.
Yin et al., "Hydrothermal Conversion of Cellulose to 5-Hydroxymethyl Fufural", International Journal of Green Energy, vol. 8, pp. 234-247, 2011.
Zhang et al., "Ionic Liquid—Water Mixtures: Enhanced Kw for Efficient Cellulosic Biomass Conversion", Energy & Fuels, vol. 24, pp. 2410-2417, 2010.
Zhang et al., "Phosphotungstic Acid Encapsulated in Metal-Organic Framework as Catalysts for Carbohydrate Dehydration to 5-Hydroxymethylfurfural", ChemSusChem, vol. 4, pp. 59-64, 2011.
Zhao et al., "One pot production of 5-hydroxymethylfurfural with high yield from cellulose by a Bronsted-Lewis-surfactant-combined heteropolyacid catalyst", Chem Commun. vol. 47, pp. 2176-2178, 2011.
International Search Report and Written Opinion pertaining to Application No. PCT/IN2019/050116 dated May 24, 2019.

PROCESS DEVELOPMENT FOR 5-HYDROXYMETHYLFURFURAL (5-HMF) SYNTHESIS FROM CARBOHYDRATES

CROSS-REFERENCES TO RELATED APPLICATIONS

This application is a national-stage application under 35 U.S.C. § 371 of International Application No. PCT/IN2019/050116, filed Feb. 14, 2019, which claims the benefit of priority to Indian Patent Application 201811023331, filed Jun. 22, 2018.

FIELD OF THE INVENTION

The present invention relates to a new protocol for process development for 5-hydroxymethylfurfural (5-HMF) synthesis from carbohydrates. A convenient, atom-economic, highly selective and cost-effective process has been developed for the preparation of 5-HMF from cellulose, hemicellulose, starch, different sources of carbohydrates and further extended to glucose and fructose.

BACKGROUND OF THE INVENTION

Since petrochemical resources of energy are going to diminish day by day. Therefore, people have been started to find out suitable pathways for their replacement with renewable resources. Biomass resources (lignocellulose, cellulose, starch, fructose, glucose, sucrose etc.) have been assumed as renewable resources for production of energy and fine bulk chemicals as these resources are widely available in nature. Biomass derived 5-hydroxymethylfurfural (HMF) is a platform intermediate for production of many bio-based bulk chemicals and fuels. 5-HMF has been assumed as a bridge between biomass resources and bio-chemicals and fuels. 5-HMF along with furfural and 2,5-furandicarboxylic acid (FDCA) were listed as most valuable bio chemicals by the US Department of Energy [(a) T. Werpy and G. Petersen, Top Value Added Chemicals from Biomass, NREL/TP-510-35523, National Renewable Energy Laboratory, Golden, Colo., 2004; (b) J. J. Bozell and G. R. Petersen, *Green Chem.*, 2010, 12, 539-554]. Less attention has been given in the field of development of efficient methods for production of HMF and its derivatives from biomass until middle of 20$^{th}$ century. The research area got more popularity after 1951, when the first review article for production of furan from carbohydrates was published by Newth (F. H. Newth, *Adv. Carbohydr. Chem.*, 1951, 6, 83-106). In 1956, Peniston first time reported biphasic solvent system wherein he reported improved 5-HMF selectivity from fructose by using n-butanol as extracting solvent. (Q. P. Peniston, U.S. Pat. No. 2,750,394, 1956). Later on B. F. M. Kuster and H. J. C. van der Steen reported MIBK-water biphasic system for synthesis of 5-HMF from fructose (B. F. M. Kuster and H. J. C. van der Steen, *Starch/Staerke*, 1977, 29, 99-103). The Kuster's finding of MIBK-water biphasic system has received much attention in later on development of 5-HMF from biomass. Meanwhile many researchers have started to synthesize 5-HMF from carbohydrates by using organic solvents. Under this study, DMSO was found to be an excellent organic solvent for 5-HMF production due to its highest solubility for carbohydrates and stability of the product.

Wang et al has reported high yielding 5-HMF (53%) synthesis from cellulose by using Cr [(DS)H$_2$PW$_{12}$O$_{40}$]$_3$ catalyst at 150° C. in single aqueous system. (S. Zhao, M. Cheng, J. Li, J. Tian and X. Wang, *Chem. Commun.*, 2011, 47, 2176-2178). Solid acids such as polytungstic acid and MOF supported PTA have also applied for 5-HMF synthesis in good yields from fructose in polar aprotic solvents [(a) K. Shimizu, R. Uozumi and A. Satsuma, *Catal. Commun.*, 2009, 10, 1849-1853; (b) A. J. Sanborn, U.S. Pat. No. 7,317,116, 2008; (c) Y. Zhang, V. Degirmenci, C. Li and E. J. M. Hensen, *Chem-SusChem*, 2011, 4, 59-64].

In 2009, Binder and Raines et al. have reported the synthesis of 5-HMF from fructose, glucose and cellulose in DMA by using metal bromides or iodides. Under this polar aprotic solvent system good yield of 5-HMF was detected (J. B. Binder and R. T. Raines, *J. Am. Chem. Soc.*, 2009, 131, 1979-1985).

Dumesic's group reported biphasic solvent system successfully for conversion of fructose to 5-HMF in good yield [(a) Y. Román-Leshkov, J. N. Chheda and J. A. Dumesic, *Science*, 2006, 312, 1933-1937; (b) J. N. Chheda, Y. Román-Leshkov and J. A. Dumesic, *Green Chem.*, 2007, 9, 342-350].

Several researchers have reported ionic liquids as solvent for dehydration of cellulose to 5-HMF in considerable yields (>50%) by using many metal catalysts at particular conditions [(a) F. Ilgen, D. Ott, D. Kralisch, C. Reil, A. Palmberger and B. König, *Green Chem.*, 2009, 11, 1948-1954; (b) P. Wang, H. Yu, S. Zhan and S. Wang, *Bioresour. Technol.*, 2011, 102, 4179-4183; (c) X. Qi, M. Watanabe, T. M. Aida and R. L. Smith Jr., *ChemSusChem*, 2010, 3, 1071-1077].

Zhang et al. have reported highest yield of HMF (89%) from cellulose by using CrCl$_2$ catalyst and [EMIM]Cl ionic liquid solvent at 120° C. for 6 h but these are not so easy processes for scale up synthesis (Y. Zhang, H. Du, X. Qian and E. Y. X. Chen, *Energy Fuels*, 2010, 24, 2410-2417).

Although the yields of 5-HMF by dehydration of fructose, glucose and polysaccharides in ionic liquids are excellent in comparison with other above discussed methods but there are limitations in their use as these are very expensive, not much stable at high temperature, difficult for scale up synthesis and difficult for separation.

Objective of the Invention

The main objective of the present invention is to develop a process for highly selective and cost-effective synthesis of 5-HMF from carbohydrates (cellulose, hemicellulose, starch, polysaccharides, glucose and fructose) which has versatile applications in the area of bio-polymer, bio-fuel and obviates the drawbacks as detailed.

Another objective of the present invention is to develop an atom-economic and high yielding approach with very less by-product formation and without tedious purification.

Yet another objective of the present invention is to develop a milder and efficient approach, applicable in scale-up transformation.

Still another objective of the present invention is to scalable process development for 5-HMF synthesis utilizing low cost carbohydrates.

Yet another objective of the present invention is to utilize non-edible and low cost cellulose/carbohydrates to high valued 5-HMF synthesis as feedstock of bio-polymer and bio-fuel.

Still another objective of the present invention is to utilize the 5-HMF to low cost 2,5-furandicarboxylic acid (FDCA) as biopolymer precursor, 2,5-dimethyl furan (DMF) as bio-fuel and commercially important molecules/products synthesis.

SUMMARY OF THE INVENTION

The present invention provides a cost-effective, atom-economic, highly-selective and high yielding approach for 5-HMF synthesis from low cost carbohydrates (such as cellulose, hemicellulose, starch, polysaccharide, glucose and fructose) following convenient and scalable approach with negligible by-product formation.

In an aspect of the invention there is described a single pot process for preparation of compound 5-HMF [5-hydroxymethylfurfural] prepared by the process wherein the process steps comprising:
  i. reacting Carbohydrates with oxalic acid and inorganic acids in presence of biphasic solvent and carbon materials at 110° C.-160° C. for 6 h-12 h under vigorous stirring condition.
  ii. dried over $Na_2SO_4$ and further solvent evaporation under reduced pressure gave compound 5-HMF [5-hydroxy methyl furfural] gave high yield of 5-HMF with high purity.

In another aspect of the invention, carbohydrates were selected from the group consisting of cellulose, polysaccharide, starch, hemicellulose, rice straw derived cellulose, potato waste starch, glucose, fructose.

In yet another aspect of the invention, the Inorganic acids selected from the group consisting of $AlCl_3$ and HCl.

In still another aspect of the invention, oxalic acid dihydrate (1 equiv.), $AlCl_3$ (10-15 wt %) and HCl (4N, 25-35 wt %) are added in equal proportion by volume to the reaction mixture.

In yet another aspect of the invention, wherein material is selected from the group consisting of activated carbon, carbon building block, material constituted with carbon, polycarbon material such as graphene and carbon nano-tube/road to reduce unwanted by-product formation, stabilized the intermediate, enhance selectivity, reduce light sensitivity and help to stabilized final product.

In still another aspect of the invention, Biphasic solvent used is [Methyl isobutyl ketone (MIBK):2-butanol (3:1)]: DMSO (1:1) to avoid unwanted reaction, enhance yield and easy purification;

In yet another aspect of the invention, final extraction and evaporation of solvent gave high yield of 5-HMF with high purity.

In still another aspect of the invention, wherein solvent used for extraction is selected from the group consisting of alkyl ketones, ethyl acetate, dichloromethane, chloroform, THF and ether.

In yet another aspect of the invention, the process involves an auto degradable oxalic acid dihydrate provides water and acidity of the system in a selective and specific manner as well as combination of inorganic acids ($AlCl_3$ and HCl) to avoid unwanted reaction and fulfill the desired condition required for successful conversion.

In still another aspect of the invention, the process is biocompatible low cost carbon material, charcoal performed significant role to hold the molecules in a proper shape and successive interaction to desired product formation in a highly-selective manner.

In yet another aspect of the invention, the carbon material used in the process also shows significant role to manage light sensitivity of the process of the system to decrease by-product formation and provide proper environment to stabilized the product.

In still another aspect of the invention, the reagent, substrate, solvent and condition altogether play significant role for the fruitful transformation of carbohydrates into 5-HMF and minimized by-product formation. Therefore, all the substrate used under the process having a combined synergistic and very specific role for this conversion.

In yet another aspect of the invention, the described method is applicable for bulk or commercial level production of 5-HMF from carbohydrates and further it could be applicable as a feedstock for bio-polymer, bio-fuel and commercially valuable products synthesis.

BRIEF DESCRIPTION OF THE INVENTION

The present invention provides "Process development for 5-hydroxymethylfurfural (5-HMF) synthesis from carbohydrates" obtained by:
  a) cellulose as a main building block starting material have been used for the construction of 5-HMF.
  b) to enhance scope of the present process, the same method is also applicable for hemicellulose, starch, polysaccharide, glucose and fructose for selective conversation of 5-HMF.
  c) biocompatible carbon material used as a facile agent to perform the whole conversion in a successful manner with high selectivity, maintain acid strength, structure stability, water balance, decolourising material and light stability to reduce by-product formation and to achieve high yield of 5-HMF synthesis.
  d) organic acid dihydrated has been used for control manner synthesis, sustainable release of water required for first level breaking of the poly-carbohydrate bonds to monomeric unit (glucose/fructose) and perform as an acid and simultaneously in situ decomposition to non/less acidic substrate which also help to improve the product yield.
  e) combined inorganic acids also used to maintain the acidity required for this conversion and simultaneously Lewis acid played significant role for in situ conversion of glucose to fructose in a control manner, required for overall synthesis.
  f) biphasic solvents have been selected to solve several problems and give highest conversion and simplicity for separation of solid materials and purification of product with less by-product formation. The best biphasic solvent combination was selected to meet high temperature, high polar, partly miscible with water, separable by washing with water and organic solvent.
  g) temperature may be selected from 100 to 140° C. to get highest yield with low by-product formation and the temperature may be variable from 80 to 180° C. based on different carbohydrates source applied for this transformation.
  h) the time may be selected from 6-20 hours or till completion of the reaction.
  i) purification majorly followed by solvent extraction and may be followed by other purification technique.
  j) in an embodiment of the present invention is described that the 5-HMF could be useful feedstock for several commercial important products synthesis. In an embodiment of the present invention 5-HMF can be used for bio-polymer [2,5-furan dicarboxylic acid (FDCA), biofuel (2,5-dimethyl furan (DMF)] and fine chemicals synthesis.
  k) in another embodiment of the present invention provides a cost-effective, atom-economic and efficient process for the synthesis of 5-HMF as a building block of several commercial important products.

l) in still another embodiment of the present invention, the process could be applicable for large scale production of 5-HMF to meet industrial demand.

DETAILED DESCRIPTION OF THE INVENTION

In an embodiment of the present invention there is provided a "Process development for 5-hydroxymethylfurfural (5-HMF) synthesis from carbohydrates" which comprises in situ steps following hydrolysis of polysaccharides to monomeric unit (glucose), isomerization of monomer i.e. glucose to fructose and dehydrative approach for 5-HMF formula 1 synthesis.

In another embodiment of the present invention there is provided aproblematic, tedious and low yielding approach of cellulose to 5-HMF synthesis in large scale process development has been solved under this method.

In yet another embodiment of the present invention there is provided aa method for the synthesis of 5-HMF starting from cellulose in a one-pot reaction, avoiding high cost reagents.

In still another embodiment of the present invention, the same process is applicable for conversion of hemicellulose, starch, raw potato waste, other polysaccharides and monomer units (such as glucose and fructose) to high yielding 5-HMF synthesis.

In yet another embodiment of the present invention, the modified synthetic approach was found to be highly selective, high yielding and applicable for large scale production of 5-HMF from different carbohydrates.

In still another embodiment of the present invention, the combined reaction media also help to restrict molecules for unusual over-reaction, improve yields and make the whole process easy to purify product, 5-HMF from reaction mixture with ~80-98% purity without tedious purification process.

In yet another embodiment of the present invention, the whole modified system also restricts unwanted polymerization and dark colour formation under reaction condition.

In still another embodiment of the present invention, the scale-up process for 5-HMF synthesis as platform compound further could be applicable for several industrially important precursors such as FDCA: 2,5-furanedicarboxylic acid, DMF: 2,5-dimethylfuran, DHMF: 2,5-dihydroxymethylfuran, DFF: 2,5-diformylfural, LA: levulinic acid and other fine chemicals synthesis for industrial or biochemical use (Scheme 1).

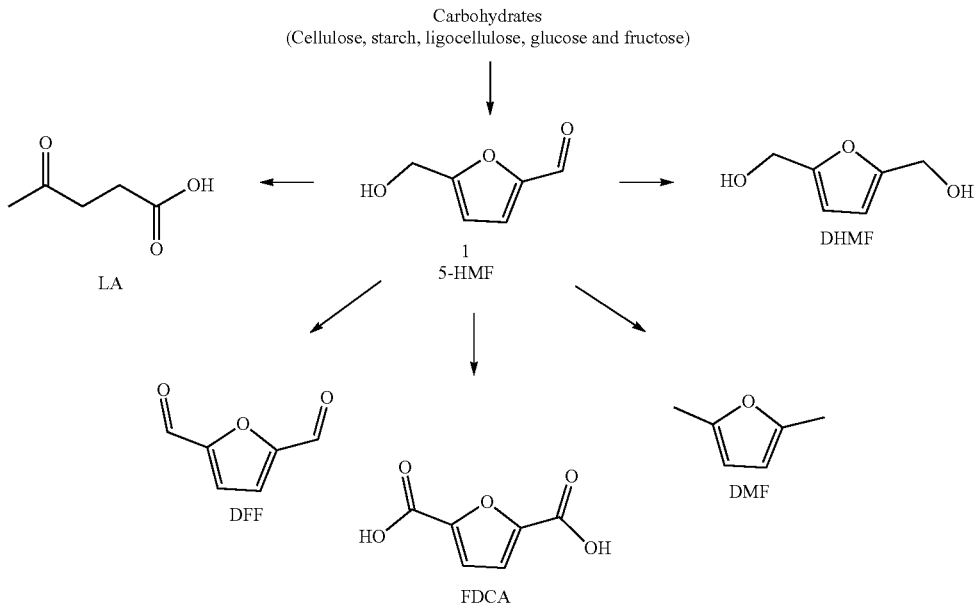

Scheme 1. 5-HMF synthesis from various carbohydrates

EXAMPLES

Following examples are given by way of illustration and therefore should not be construed to limit the scope of the invention. In the present invention, Rice straw derived cellulose obtained from Oryza Sativa plant Family: Gramineae and Purchased from farmer field, Village & post office: Trehal, Tehsil-Baijnath, Dist-Kangra, Pin-176061, H.P, whereas waste Raw Potato [Solanum Tuberosum; Family: Solanaceae] purchased from Raj Kumar, Krishan Lals Co. Fruits & Vegetables, Commission agents, Shop No. 2, New Sabzi Mandi, Palampur-176061, H.P. Cellulose, starch and fructose purchased from CDH Pvt. Ltd. Corp. Office, 7/28 Vardaan House, Daryaganj, New Delhi-110002 and Glucose purchased from Sigma Aldrich Chemicals Pvt. Ltd, Plot-12, Banglore-560100

General Experimental Description:

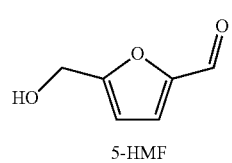

5-HMF

An oven dried round bottomed flask was charged with equivalent amount of carbohydrate (1 equiv.) and oxalic acid dihydrate (1 equiv.). Then 10-15 wt % $AlCl_3$, 20-30 wt % activated charcoal, 25-35 wt % HCl (4N), MIBK:2-butanol (3:1) and DMSO were added in equal proportion by volume to the reaction mixture and heated at 100-160° C. for 6-12 h under vigorous stirring condition. The compound 1 (5-HMF) was extracted from reaction mixture by ethyl acetate/$CHCl_3$/$CH_2Cl_2$, dried over $Na_2SO_4$ and evaporated under reduced pressure.

Example 1

Cellulose to 5-HMF Synthesis:
An oven dried round bottomed flask (500 mL) was charged with cellulose powder (20 g), oxalic acid dihydrate (20 g), $AlCl_3$ (3 g), activated charcoal (4 g), HCl (4N, 18 mL), MIBK: 2-butanol (90:30) mL and DMSO (120 mL) and heated at 110° C. for 6 h under vigorous stirring condition. The compound 1 (5-HMF) was extracted from reaction mixture by ethyl acetate, dried ($Na_2SO_4$) and evaporated under reduced pressure gave compound 1, 13.00 g (65 wt %, 93 mol %$^a$). $^1$H NMR (300 MHz, $CDCl_3$) δ 9.37 (s, 1H), 7.12 (d, J=3.5 Hz, 1H), 6.39 (d, J=3.5 Hz, 1H), 4.55 (s, 2H); $^{13}$C NMR (300 MHz, $CDCl_3$) δ 177.65, 161.03, 151.72, 123.49, 109.71, 56.84; m/z MS (ESI) $[M+1]^+$=127, $[M+1-H_2O]^+$=109, $[M+1-H_2O—CO]^+$=81

Example 2

Starch to 5-HMF Synthesis:
An oven dried round bottomed flask (500 mL) was charged with starch (20 g), oxalic acid dihydrate (20 g), $AlCl_3$ (3 g), activated charcoal (4 g), HCl (4N, 18 mL), MIBK:2-butanol (90:30) mL and DMSO (120 mL) and heated at 110° C. for 6 h under vigorous stirring condition. The compound 1 (5-HMF) was extracted from reaction mixture by ethyl acetate, dried ($Na_2SO_4$) and evaporated under reduced pressure gave compound 1, 12.80 g (64 wt %, 92 mol %$^a$) in sufficiently pure form. The spectral data was same as mentioned for compound 1 (Experimental description 1).
Mole percent yield was calculated with respect to glucose monomer.

Example 3

Raw Potato Waste to 5-HMF Synthesis:
An oven dried round bottomed flask (250 mL) was charged with dried raw potato (15.45 g), oxalic acid dihydrate (13.50 g), $AlCl_3$ (2.025 g), activated charcoal (2.700 g), HCl (12N, 1.745 mL), MIBK:2-butanol (45:15) mL and DMSO (60 mL) and heated at 110° C. for 6 h under vigorous stirring condition. The compound 1 (5-HMF) was extracted from reaction mixture by ethyl acetate, dried ($Na_2SO_4$) and evaporated under reduced pressure gave compound 1, 10.28 g (66 wt %). The spectral data was same as mentioned for compound 1 (Experimental description 1).

Example 4

Rice Straw Derived Cellulose to 5-HMF Synthesis:
An oven dried round bottomed flask (100 mL) was charged with rice straw derived cellulose (1 g), oxalic acid dihydrate (1 g), $AlCl_3$ (150 mg), activated charcoal (200 mg), HCl (4N, 0.9 mL), MIBK:2-butanol (4.5:1.5) mL and DMSO (6 mL) and heated at 110° C. for 12 h under vigorous stirring condition. The compound 1 (5-HMF) was extracted from reaction mixture by ethyl acetate, dried ($Na_2SO_4$) and evaporated under reduced pressure gave compound 1, 0.350 g (35 wt %). The spectral data was same as mentioned for compound 1 (Experimental description 1).

Example 5

Glucose to 5-HMF Synthesis:
An oven dried round bottomed flask (100 mL) was charged with glucose (1 g), oxalic acid dihydrate (1 g), $AlCl_3$ (150 mg), activated charcoal (200 mg), HCl (4N, 0.9 mL), MIBK:2-butanol (4.5:1.5)) mL and DMSO (6 mL) and heated at 110° C. for 6 h under vigorous stirring condition. The compound 1 (5-HMF) was extracted from reaction mixture by ethyl acetate, dried ($Na_2SO_4$) and evaporated under reduced pressure gave compound 1, 0.650 g (65 wt %, 93 mol %). The spectral data was same as mentioned for compound 1 (Experimental description 1).

Example 6

Fructose to 5-HMF Synthesis:
An oven dried round bottomed flask (100 mL) was charged with fructose (1 g), oxalic acid dihydrate (1 g), $AlCl_3$ (150 mg), activated charcoal (200 mg), HCl (4N, 0.9 mL), MIBK:2-butanol (4.5:1.5) mL and DMSO (6 mL) and heated at 110° C. for 6 h under vigorous stirring condition. The compound 1 (5-HMF) was extracted from reaction mixture by ethyl acetate, dried ($Na_2SO_4$) and evaporated under reduced pressure gave compound 1, 0.642 g (64 wt %, 92 mol %). The spectral data was same as mentioned for compound 1 (Experimental description 1).

ADVANTAGE OF THE INVENTION

1. A simple, atom-economic and cost-effective process has been developed for the preparation of 5-HMF from carbohydrates.
2. Carbohydrates preferably low cost cellulose could be applicable for large-scale production of 5-HMF avoiding harsh reaction condition and tedious purification with high yield.
3. Easy scalable process and purification reduces production cost of 5-HMF assertively.
4. Easy purification and no need of traditional column chromatography, reduces production cost assertively.
5. The process could be applicable for low cost production of highly demanding platform compound 5-HMF and further industrially important high value molecules such as DHMF, DMF, FDCA, DFF and LA.
6. The process could be applicable for low cost production of biopolymer and biofuel from carbohydrates.

The invention claimed is:
1. A single-pot process for the preparation of 5-hydroxymethylfurfural, the single-pot process comprising:
reacting carbohydrates with oxalic acid and inorganic acids in the presence of a biphasic solvent and a carbon material at a temperature from 110° C. to 160° C. for a time period of from 6 hours to 12 hours under vigorous stirring to form a reaction mixture; and
drying the reaction mixture over $Na_2SO_4$; and
evaporating solvent from the reaction mixture under reduced pressure to yield the 5-hydroxymethylfurfural.
2. The single-pot process of claim 1, wherein the carbohydrates are selected from the group consisting of cellulose, polysaccharide, starch, hemicellulose, cellulose derived from rice straw, potato waste starch, glucose, and fructose.

3. The single-pot process of claim 1, wherein the inorganic acid is selected from $AlCl_3$ and HCl.

4. The single-pot process of claim 1, wherein the reaction mixture comprises:
   oxalic acid dihydrate at a molar concentration of 1 equivalent;
   from 10% to 15% by weight $AlCl_3$; and
   from 25% to 35% by weight HCl (4N),
wherein the oxalic acid dihydrate, the $AlCl_3$, and the HCl (4N) are added to the reaction mixture in equal proportion by volume.

5. The single-pot process of claim 1, wherein the carbon material is selected from the group consisting of activated carbon, carbon building block, material constituted with carbon, polycarbon material, graphene, carbon nanotubes, and carbon nanorods.

6. The single-pot process of claim 1, wherein the biphasic solvent is selected from the group consisting of methyl isobutyl ketone, 2-butanol, and dimethylsulfoxide.

7. The single-pot process of claim 1, wherein evaporating solvent from the reaction mixture further comprises:
   performing an extraction with an extraction solvent selected from the group consisting of alkyl ketones, ethyl acetate, dichloromethane, chloroform, tetrahydrofuran, and ether; and
   evaporating the extraction solvent.

* * * * *